United States Patent [19]

Novello et al.

[11] 3,963,731

[45] June 15, 1976

[54] PYRIDYL CONTAINING 1-BENZENESULFONYL TRIAZOLES

[75] Inventors: Frederick C. Novello, Berwyn; John J. Baldwin, Lansdale, both of Pa.

[73] Assignee: Merck & Co., Inc., Rahway, N.J.

[22] Filed: Feb. 6, 1975

[21] Appl. No.: 547,847

Related U.S. Application Data

[60] Division of Ser. No. 361,915, May 21, 1973, Pat. No. 3,892,762, which is a continuation-in-part of Ser. No. 75,784, Sept. 25, 1970, abandoned.

[52] U.S. Cl. .......................................... 260/294.8 F
[51] Int. Cl.² ......................................... C07D 249/08
[58] Field of Search ............................. 260/294.8 F

[56] References Cited
UNITED STATES PATENTS 3,892,762   7/1975   Baldwin et al. ................ 260/294.8 F

OTHER PUBLICATIONS

Baldwin et al., "Chem. Abstracts" vol. 77, (1972), No. 5487.

*Primary Examiner*—Henry R. Jiles
*Assistant Examiner*—R. W. Ramsuer
*Attorney, Agent, or Firm*—Daniel T. Szura; J. Jerome Behan

[57]   ABSTRACT

Compositions useful in the treatment of gout and hyperuricemia and containing a substituted 1,2,4-triazole as the active ingredient are provided, the triazoles being substituted at the 5 position with a pyridyl radical and at the 3 position with a phenyl or a pyridyl radical. Methods of preparing these substituted triazoles are described. Certain of the compounds are novel.

3 Claims, No Drawings

PYRIDYL CONTAINING 1-BENZENESULFONYL TRIAZOLES

This is a division of our copending U.S. Pat. application Ser. No. 361,915, filed May 21, 1973 now U.S. Pat. No. 3,892,762 which in turn is a continuation-in-part of U.S. application Ser. No. 75,784, filed Sept. 25, 1970, now abandoned.

BACKGROUND OF THE INVENTION

1. Field of the Invention

The invention relates to the use of certain 1,2,4-triazoles which are substituted in the 3 and 5 positions, and which may optionally be substituted in the 1 position as antigout and anti-hyperuricemic agents.

2. Description of the Prior Art

The herein-described 3,5-di-substituted-1,2,4-triazoles have utility as anti-gout and anti-hyperuricemic agents.

Gout is a condition affecting humans and lower animals, which is characterized by perversion of the purine metabolism resulting in hyperuricemia, i.e., an excess of uric acid in the blood, attacks of acute arthritis, and formation of chalky deposits in the cartilages of the joints. These deposits are made up chiefly of urates, or uric acid.

Uric acid serves no biochemical function in the body and is merely an end product of purine metabolism. It is well known in the art that the purine bases adenine and guanine, which play key roles in a wide variety of chemical processes, both give rise to uric acid in the body. Adenylic acid and guanylic acid are converted to the free purine bases by destructive metabolic enzymes. A portion of the free purine bases is converted to purine ribonucleotides and the remainder is degraded to the free bases xanthine and hypoxanthine. A single enzyme, xanthine oxidase, converts both xanthine and hypoxanthine to uric acid for excretion.

Although human purine biosynthesis can be inhibited at the stage of formyl glycinimide ribotide by the glutamine antagonists azaserine and 6-diazo-5-oxo-1-norleucine, a high incidence of undesirable side effects precludes their being used clinically for this purpose. In recent years, substantial progress has been made in attempting to control the excessive levels of uric acid in patients afflicted with gout through the use of pharmaceutical agents. Uric acid synthesis has been effectively blocked by the use of allopurinol, i.e., 4-hydroxypyrazolo-[3,4-d]-pyrimidine, a compound which is a structural isomer of hypoxanthine. Ahopurinol acts as a specific inhibitor of the enzyme xanthine oxidase, which is responsible for the conversion of both hypoxanthine and xanthine to uric acid. As a direct result of the administration of this compound to patients afflicted with gout, part of the uric acid which would normally end up in the urine is replaced by the oxypurines, hypoxanthine and xanthine, thus greatly reducing the content of uric acid in serum and urine. Azathioprine has also been used to inhibit excessive purine synthesis, and thus reduce the abnormally high amounts of uric acid found in the serum and urine of afflicted patients. Other compounds, such as acetylsalicyclic acid, thiophenylpyrazolidine and phenylbutazone have been employed in the treatment of gout. Many of the existing compounds used in the treatment of gout, however, relieve the inflammation and other symptoms connected therewith but have no effect on the conditions which give rise to gouty arthritis or hyperuricemia.

Thus, there is still a need for compounds which can be employed in the prophylactic treatment of gout as well as for the treatment of other abnormal conditions associated with hyperuricemia.

SUMMARY OF THE INVENTION

According to this invention it has been found that compounds of the Formulas Ia and Ib

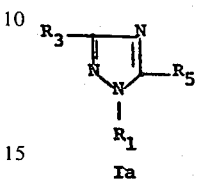

Ia

Ib where $R_1$ represents hydrogen, loweralkyl, lower alkanoyl, benzene sulfonyl, carbamoyl or loweralkyl carbamoyl, $R_3$ represents phenyl, loweralkylphenyl, pyridyl or lower alkyl pyridyl, and $R_5$ represents pyridyl or loweralkyl pyridyl; are useful as anti-gout and anti-hyperuricemic agents in that they inhibit the action of xanthine oxidase and thus reduce the uric acid content of serum and urine. Also useful for the same purpose are the N-oxides and pharmaceutically acceptable non-toxic acid salts of such compounds, the N-oxides and the salts being of the pyridine ring present in the molecule.

These compounds also possess useful hypotensive activity and some of the compounds exhibit bronchodilating properties.

There are provided pharmaceutical compositions containing these substances as anti-gout, anti-hyperuricemic and hypotensive agents, and the method of treating gout, hyperuricemia and of lowering blood pressure by the administration of effective amounts of such compounds and compositions containing them to a host requiring them.

Certain of these compounds are novel, for example, the N-oxides, those wherein $R_1$ is other than hydrogen, and those where $R_5$ is other than 4-pyridyl, and the invention contemplates providing these novel compounds and methods of preparing them.

DESCRIPTION OF THE PREFERRED EMBODIMENTS

The preferred compounds to be used in the compositions and methods of this invention as anti-gout, anti-hyperuricemic and hypotensive agents are those of Formulas Ia and Ib above wherein $R_1$ is hydrogen, a loweralkyl radical and preferably one containing from 1–5 carbons, saturated or unsaturated, such as methyl, ethyl, butyl, amyl, propenyl or propargyl, a loweralkanoyl radical and preferably one of 2–6 carbons such as acetyl, propionyl, butyryl, benzenesulfonyl, a carbamoyl or diloweralkylcarbamoyl radical where the loweralkyls are preferably methyl, ethyl or propyl. In the most preferred aspect of the invention, $R_1$ is hydrogen.

$R_3$ represents a phenyl or alkylphenyl radical which may have from 1–3 alkyl substituents which are preferably loweralkyl such as methyl, ethyl, or butyl. It also represents pyridyl or loweralkyl pyridyl, the latter containing from 1 to 3 loweralkyl groups which may be the same or different and preferably are methyl, ethyl or propyl. The pyridyl or alkylpyridyl substituent may be any one of the three possible isomers. In the most preferred aspects of the invention, $R_3$ is phenyl or 4-pyridyl.

$R_5$ can be pyridyl or loweralkyl pyridyl as described for the $R_3$ substituent. The preferred compounds are those wherein $R_5$ is 4-pyridyl.

Included within the scope of the invention are the pharmaceutically acceptable salts of these 1,2,4-triazoles. They include the alkali and alkaline earth metal salts such as the sodium, potassium and calcium. Also included are the acid addition salts and quaternary salts of the pyridyl nitrogen, examples being the methiodides, ethiodides, hydrochlorides, sulfates, tartrates, oxalates and the like. N-oxides of the pyridyl substituents are also within the scope of the invention.

As previously stated, the foregoing compounds have the property of reducing the concentration of uric acid in blood and urine, and also of reducing blood pressure. These therapeutically active compounds are administered to mammals requiring such treatment admixed with or intimately dispersed in a pharmaceutically acceptable carrier, preferably in the form of a solid, orally administrable, unit dosage form such as tablets, or capsules, or as solutions or suspensions of the type represented by syrups and elixers. The amount of active ingredient in the pharmaceutical composition may be varied within reasonable limits depending upon such factors as pharmaceutical elegance and the amount of drug desired at each administration. It is convenient to employ solid unit dosage formulations containing from about 25–500 milligrams of active ingredient, and liquid preparations containing from about 5–40% by weight of triazole.

These pharmaceutical compositions may be made by any of the known pharmaceutical methods. For example, for tablets the triazoles are compounded with an inert pharmaceutical carrier which may contain a suitable binder such as, for example, gums, starches, and sugars. They may also be incorporated into a gelatin capsule with or without a diluent, or formulated into elixirs, syrups or suspensions which have the advantage of being susceptible to manipulations in flavor by the addition of standard natural or synthetic flavoring materials. The compound is generally administered in compositions which are so proportioned as to afford a dosage of about 30 mg. to 1.5 gm. per day as the effective amount. The preferred oral dosage level is about 100–800 mg. per day.

The following examples serve to illustrate typical tablet, capsule, and elixir formulations containing the therapeutically active triazoles of this invention.

FORMULATION I:
COMPRESSED TABLET COMPRISING
0.5 GM. OF ACTIVE INGREDIENT

| INGREDIENT | AMOUNT-MG. |
|---|---|
| 3-(3-pyridyl)-5-(4-pyridyl)-1,2,4-triazole | 500.0 |
| Starch paste- 12½%, 100 cc. allow. | 12.5 |
| | 512.5 |
| Starch, U.S.P. Corn | 25.0 |
| Magnesium stearate | 5.5 |
| | 543.0 |

The 3-(3-pyridyl)-5-(4-pyridyl)-1,2,4-triazole is granulated with the starch paste and while moist passed through a No. 14 screen, dried at 45°C. for 20 hours, and then passed 3 times through a No. 14 screen. The starch is then passed through a No. 90 bolting cloth onto the granulation, and all ingredients are blended thoroughly. The magnesium stearate is passed through a No. 90 bolting cloth onto the granulation, and these ingredients are blended, after which the granulation is compressed into tablets using a 14/32 inch flat, bevelled, scored punch having a thickness of 0.025 ±0.005 inch yielding 1,000 tablets each weighing 0.543 grams.

A similar tablet containing 3,5-di-(4-pyridyl)-1,2,4-triazole is prepared by following the above procedure and using the di-(4-pyridyl)-triazole as active ingredient.

| FORMULATION II: ENCAPSULATION - FOR 350 MG. CAPSULE | |
|---|---|
| INGREDIENT | AMOUNT - MG. |
| 3-phenyl-5-(4-pyridyl)-1,2,4-triazole | 250 |
| Lactose | 93 |
| Talc | 7 |

The lactose, talc and the 3-phenyl-5-(4-pyridyl)-1,2,4-triazole are blended in suitable blending equipment, and encapsulated into a No. 2 capsule at a target weight of 350 mg.

| FORMULATION III: LIQUID SUSPENSION - FORMULA | |
|---|---|
| INGREDIENT | AMOUNT-g./l. |
| Veegum H.V. | 3.0 |
| Water | 150.0 |
| Methyl paraben | 1.0 |
| 1-methyl-3,5-di(4-pyridyl)-1,2,4-triazole | 50.0 |
| Kaolin | 10.0 |
| Flavor | 1.0 |
| Glycerin, 9.5 to 1 liter | |

Suspend Veegum in water with vigorous agitation, add methyl, paraben and allow to stand overnight to ensure complete hydration of Veegum. In separate vessel suspend 1-methyl-3,5-di-(4-pyridyl)-1,2,4-triazole in about 750 cc. of glycerin. Add kaolin and stir until homogeneous. Slowly add aqueous dispersion of Veegum and methyl paraben. Add flavor and continue agitation for 1 hour to ensure homogeneity. Q.S. with remaining glycerin to 1:1. Stir until homogeneous. 1 Teaspoonful contains 250 mg. of 1-methyl-3,5-di-(4-pyridyl)-1,2,4-triazole.

Representative compounds which are part of the present invention which may be formulated as described above are:
3,5-di(2-pyridyl)-1,2,4-triazole,
5-(4-pyridyl)-3-(2-methyl-4-pyridyl)-1,2,4-triazole,
3,5-di(2-methyl-4-pyridyl)-1,2,4-triazole,
5-(4-pyridyl)-3-(2,6-dimethyl-4-pyridyl)-1,2,4-triazole,
3,5-di(2,6-dimethyl-4-pyridyl)-1,2,4-triazole,
1-butyryl-3,5-di(4-pyridyl)-1,2,4-triazole,
1-acetyl-3,5-di(4-pyridyl)-1,2,4-triazole,
1-ethyl-3,5-di(2-pyridyl)-1,2,4-triazole,
1-carbamoyl-3,5-di(2-pyridyl)-1,2,4-triazole,
3,5-di(4-pyridyl)-1,2,4-triazole,
3-phenyl-5-(4-pyridyl-N-oxide)-1,2,4-triazole,
3,5-di(4-pyridyl)-1,2,4-triazole hydrochloride, and 3-(2,4,6-trimethylphenyl)-5-(2-methyl-5-ethyl-4-pyridyl)-1,2,4-triazole sulfate.

The compounds of Formulas Ia and Ib can be prepared by the series of reactions set forth in the following flow diagram:

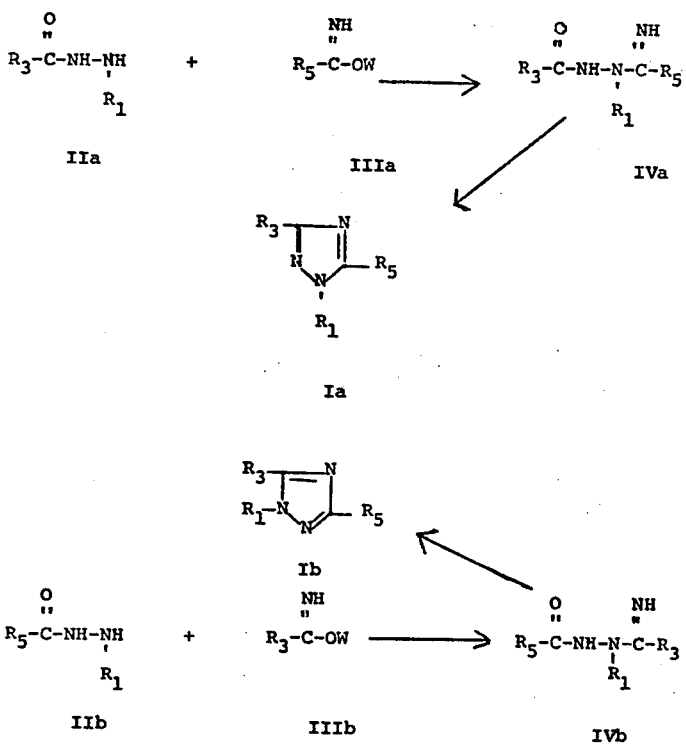

wherein $R_1$ is hydrogen or alkyl and $R_3$ and $R_5$ are as defined above, and W is a lower alkyl group containing 1–5 carbons.

As can be seen from the above reaction scheme, a substituted hydrazide compound such as, for example, an acid hydrazide of formula IIa or IIb is reacted with an imino ester of formula IIIa or IIIb in a suitable solvent. Either low boiling solvents such as methanol, ethanol, or nitromethane, or high boiling solvents such as decalin, xylene or dimethylsulfoxide may be employed. When low boiling solvents are used, the product of the reaction is usually the intermediate acylamidrazone IVa or IVb. A reaction time of 3–20 hours at temperatures from room temperature to the reflux temperature of the solvent is employed. Depending upon the nature of the $R_1$ substituent, either the final cyclized product is obtained or the intermediate acylamidrazone. In the case where the intermediate acylamidrazone is obtained, the intermediate may be heated without solvent at about 100°–300°C. for from about 15 minutes to several hours, or it may be heated in a high boiling solvent at a temperature from about 100°–200°C. for about 1–20 hours.

The final cyclized product is isolated and purified by techniques known in the art. When high boiling solvents are employed, the reaction is conveniently carried out at or near the reflux temperature of the solvent. The preferred temperature range is between 100°–200°C. The reaction time is dependent upon the particular temperature range employed. The reaction is carried out without isolation of the intermediate and the final cyclized product is isolated and purified by techniques known in the art. For example, the product may be crystallized from a suitable solvent, such as methanol or ethanol. As can be seen from the above reaction diagram, where $R_1$ is alkyl, the selection of the particular hydrazide compound and the particular imino ester will depend upon whether the alkyl substituent is desired adjacent to the $R_3$ or $R_5$ substituent.

Compounds having a substituent in the 1-position can also be prepared by reacting the 3,5-di-substituted triazole with an appropriate alkylating, acylating or carbamoylating agent. Where $R_3$ and $R_5$ are both different substituents, a mixture of compounds is obtained, i.e., the $R_1$ substituent may be attached to either one of the adjacent nitrogens in the triazole ring. For example, where the $R_1$ substituent is a lower alkanoyl group such as an acetyl or butyryl group, the triazole is reacted with a lower alkyl anhydride such as, for example, acetic anhydride or butyric anhydride. Where the $R_1$ substituent is an alkyl group, alkylation is achieved by reacting the sodium salt of the triazole with an alkylating agent such as, for example, dimethylsulfate. Alkylation of the 1,2,4-triazoles generally occurs in the 1-position. Where the alkyl group is a methyl group, methylation can be achieved by reacting the triazole with diazomethane in a suitable solvent, such as diethylether. The 1-carbamoyl compounds can be synthesized by reacting the sodium salt of the triazole with carbamoyl halide or di-lower alkyl carbamoyl halide in an inert solvent such as tetrahydrofuran.

The following examples are given for the purpose of illustration and not by way of limitation.

EXAMPLE 1

5-(4-PYRIDYL)-3-(2-METHYL-4-PYRIDYL)-1,2,4-TRIAZOLE

Sodium (0.4 grams) is added to 4-cyanopyridine (8.3 grams, 0.08 mole) in methanol, and the solution is allowed to stand 30 minutes at room temperature. A suspension of 2-methylisonicotinic acid hydrazide (0.07 mole) in methanol (160 ml.) is added, and the resulting solution is heated at reflux for 30 minutes. After cooling, the intermediate acylamidrazone is collected by filtration. The acyclic intermediate is then heated at 260°C. for 15 minutes, after which the reaction is cooled to room temperature. Upon recrystallization from acetonitrile-water, 5-(4-pyridyl)-3-(2-methyl-4-pyridyl)-1,2,4-triazole is obtained, m.p. 245°–248°C.

EXAMPLES 2 – 9

The following compounds are prepared by the reaction procedure described in Example 1.

EXAMPLES 2–9

| EXAMPLE | HYDRAZIDE | NITRILE | COMPOUND | MELTING POINT |
|---|---|---|---|---|
| 2 | 2-methylisonicotinic acid hydrazide | 2-methyl-4-cyanopyridine | 3,5-bis(2-methyl-4-pyridyl)-1,2,4-triazole | 229–231°C. |
| 3 | isonicotinic acid hydrazide | 2,6-dimethyl-4-cyano-pyridine | 5-(4-pyridyl)-3-(2,6-dimethyl-4-pyridyl)-1,2,4-triazole | 292–293°C. |
| 4 | 2,6-dimethylisonicotinic acid hydrazide | 2,6-dimethyl-4-cyano-pyridine | 3,5-bis(2,6-dimethyl-4-pyridyl)-1,2,4-triazole | 313–314°C. |
| 5 | nicotinic acid hydrazide | 2-cyanopyridine | 3-(2-pyridyl)-5-(3-pyridyl)-1,2,4-triazole | 246.5–248°C. |
| 6 | isonicotinic acid hydrazide | 2-cyanopyridine | 3-2-pyridyl)-5-(4-pyridyl)-1,2,4-triazole | 260–261°C. |
| 7 | nicotinic acid hydrazide | 3-cyanopyridine | 3,5-di(3-pyridyl)-1,2,4-triazole | 223–225°C. |
| 8 | p-toluic acid hydrazide | 4-cyanopyridine | 3-(p-tolyl)-5-(4-pyridyl)-1,2,4-triazole | 226–228°C. |
| 9 | isonicotinic acid hydrazide | 4-cyanopyridine-N-oxide | 5-(4-pyridyl)-3-(4-pyridyl-1-oxide)-1,2,4-triazole | 332–334.5°C. |

EXAMPLE 10

1-BUTYRYL-3,5-DI(4-PYRIDYL)-1,2,4-TRIAZOLE 3,5-Di(4-pyridyl)-1,2,4-triazole (0.5 grams) is added to butyric anhydride (10 ml.), and the reaction mixture is heated at steam bath temperatures for 20 hours. The resulting solution is concentrated until a solid separates out of solution, and the solid is collected by filtration. Upon recrystallization from hexane, 1-butyryl-3,5-di(4-pyridyl)-1,2,4-triazole is obtained, m.p. 116°–118°C.

When in the above procedure acetic anhydride is employed in place of butyric anhydride, 1-acetyl-3,5-di-(4-pyridyl)-1,2,4-triazole is obtained, m.p. 155.5°–158°C.

When in the above procedure propionic anhydride is employed in place of butyric anhydride, 1-propionyl-3,5-bis-(4-pyridyl)-1,2,4-triazole is obtained.

EXAMPLE 11

1-METHYL-3,5-DI(4-PYRIDYL)-1,2,4-TRIAZOLE

To a solution of 4-cyanopyridine (4.1 grams, 0.04 mole) in methanol (60 ml.) is added sodium (0.2 grams). The resulting solution is allowed to stand at room temperature for ½ hour and is then added to a solution of N-methylisonicotinic acid hydrazide (6 grams, 0.04 mole) in methanol (80 ml.). The solution is refluxed for 3 hours and is then concentrated until a solid separates out of solution. The solid is collected by filtration and, upon recrystallization from ethanol, 1-methyl-3,5-di(4-pyridyl)-1,2,4-triazole is obtained, m.p. 168°–170°C.

EXAMPLE 12

1-METHYL-3-(4-PYRIDYL)-5-(4-PYRIDYL-1-OXIDE)-1,2,4-TRIAZOLE

To a solution of 4-cyanopyridine-N-oxide (4.1 grams, 0.04 mole) in methanol (60 ml.) is added sodium (0.2 grams). The resulting solution is allowed to stand at room temperature for ½ hour and is then added to a solution of 1-isonicotinoyl-2-methylhydrazine (6 grams, 0.04 mole) in methanol (80 ml.). The solution is refluxed for 3 hours and is then concentrated until a solid separates out of solution. The solid is collected by filtration, and, upon recrystallization from ethanol, 1-methyl-2-(4-pyridyl)-5-(4-pyridyl-1-oxide)-1,2,4-triazole is obtained, m.p. 219°–221°C.

EXAMPLE 13

1-BENZENSULFONYL-3,5-DI(4-PYRIDYL)-1,2,4-TRIAZOLE

To 1.06 g. (0.005 mole) of 3,5-di(4-pyridyl)-1,2,4-triazole in 100 ml. of tetrahydrofuran is added 57% sodium hydride in mineral oil (0.21 g., 0.005 mole). The reaction mixture is heated at reflux for ½ hour, cooled and a solution of benzenesulfonyl chloride (0.88 g., 0.005 mole) is added. The reaction mixture is heated at reflux for ½ hour, cooled, filtered and concentrated to a solid. After recrystallization from acetonitrile 0.4 g. of 1-benzenesulfonyl-3,5-di(4-pyridyl)-1,2,4-triazole melting at 210°–212°C. is obtained.

EXAMPLE 14

1-DIMETHYLCARBAMOYL-3,5-DI(4-PYRIDYL)-1,2,4-TRIAZOLE

To 2.13 g. (0.01 mole) of 3,5-di(4-pyridyl)-1,2,4-triazole in 200 ml. of tetrahydrofuran is added 57% sodium hydride in mineral oil (0.42 g., 0.01 moles). The reaction mixture is heated at reflux for 1 hour, cooled and a solution of dimethylcarbamoyl chloride (1 g., 0.01 mole) in 10 ml. of tetrahydrofuran is added dropwise. The reaction mixture is heated at reflux for 4 hours, cooled, filtered and concentrated to an oil which solidifies. After recrystallization from benzene 1.2 g. of 1-dimethylcarbamoyl-3,5-di(4-pyridyl)-1,2,4-triazole melting at 140°–141.5°C. is obtained.

EXAMPLE 15

1-METHYL-3-(p-CHLOROPHENYL)-5-(3-PYRIDYL)-1,2,4-TRIAZOLE

To 3-cyanopyridine (2 g.) in methanol (30 ml.) is added sodium (0.1 g.). The solution is allowed to stand 0.5 hours at ambient temperature and is then added to a solution of 1-methyl-2-(p-chlorobenzoyl)hydrazine (3.6 g.) in methanol (40 ml.). The reaction mixture is heated at reflux for 5 hours and is then concentrated to an oil which solidifies. After recrystallization from isopropanol, yielding 0.2 g. of 1-methyl-3-(p-chlorophenyl)-5-(3-pyridyl)-1,2,4-triazole, m.p. 157°–158.5°C. is obtained.

EXAMPLE 16

1-METHYL-3-(p-CHLOROPHENYL)-5-(4-PYRIDYL)-1,2,4-TRIAZOLE

When 4-cyanopyridine is used in place of 3-cyanopyridine in the process described in Example 15, 1-methyl-3-(p-chlorophenyl)-5-(4-pyridyl)-1,2,4-triazole is obtained which melts at 191°C.

EXAMPLE 17

1-METHYL-3-(3-PYRIDYL)-5-(4-PYRIDYL)-1,2,4-TRIAZOLE

To 4-cyanopyridine (2 g.) in methanol (30 ml.) is added sodium (0.1 g.). The solution is allowed to stand 0.5 hours at ambient temperature and is then added to a solution of 1-methyl-2-nicotinoyl-hydrazine (3 g.) in methanol (30 ml.). The reaction mixture is heated 5 hours at reflux and is concentrated to an oil which solidifies. After chromatography on silica gel and recrystallization from acetonitrile 0.8 g. of 1-methyl-3-(3-pyridyl)-5-(4-pyridyl)-1,2,4-triazole melting 132°–133°C is obtained.

EXAMPLE 18

1-METHYL-3,5-BIS(3-PYRIDYL)-1,2,4-TRIAZOLE

When 3-cyanopyridine is used in place of 4-cyanopyridine in the process of Example 17, 1-methyl-3,5-bis(3-pyridyl)-1,2,4-triazole is obtained melting at 148°–149°C.

EXAMPLE 19

1-METHYL-3-PHENYL-5-(3-PYRIDYL)-1,2,4-TRIAZOLE

To 3-cyanopyridine (2 g.) in methanol (30 ml.) is added sodium (0.1 g.). The solution is allowed to stand 0.5 hours at ambient temperature and is then added to a solution of 1-methyl-2-benzoylhydrazine (3 g.) in methanol (40 ml.). The solution is heated 5 hours at reflux and is then concentrated to an oil which solidifies. After chromatography on silica gel and recrystallization from a mixture of acetonitrile and water, there is obtained 200 mg. of 1-methyl-3-phenyl-5-(3-pyridyl)-1,2,4-triazole, m.p. 97°–98°C.

EXAMPLE 20

1-METHYL-3-PHENYL-5-(2-PYRIDYL)-1,2,4-TRIAZOLE

When 2-cyanopyridine is used in place of 3-cyanopyridine in the process of Example 19, 1-methyl-3-phenyl-5-(2-pyridyl)-1,2,4-triazole is obtained, m.p. 105.5°–107.5°C.

EXAMPLE 21

1-METHYL-3-PHENYL-5-(4-PYRIDYL)-1,2,4-TRIAZOLE

When 4-cyanopyridine is used in place of 3-cyanopyridine in the process of Example 19, 1-methyl-3-phenyl-5-(4-pyridyl)-1,2,4-triazole is obtained, m.p. 132°–134°C.

EXAMPLE 22

1-METHYL-3-(4-PYRIDYL)-5-(2-PYRIDYL)-1,2,4-TRIAZOLE

To 2-cyanopyridine (2 g.) in methanol (30 ml.) is added sodium (0.1 g.). The solution is allowed to stand 0.5 hours at ambient temperature and is then added to a solution of 1-methyl-2-isonicotinoylhydrazine (3 g.) in methanol (50 ml.). The solution is heated at reflux 4 hours and concentrated to a gum. After chromatography on silica gel and recrystallization from acetonitrile-water 450 mg. of 1-methyl-3-(4-pyridyl)-5-(2-pyridyl)-1,2,4-triazole are obtained, melting at 145°–146°C.

EXAMPLE 23

1-METHYL-3(4-PYRIDYL)-5-(2,6-DIMETHYL-4-PYRIDYL)-1,2,4-TRIAZOLE

When 2,6-dimethyl-4-cyanopyridine is used in place of 2-cyanopyridine in the process of Example 22, 1-methyl-3(4-pyridyl)-5-(2,6-dimethyl-4-pyridyl)-1,2,4-triazole is obtained, m.p. 176°–178°C.

EXAMPLE 24

1-METHYL-3(4-PYRIDYL)-5-(3-PYRIDYL-1,2,4-TRIAZOLE

When 3-cyanopyridine is used in place of 2-cyanopyridine in the process of Example 22, 1-methyl-3(4-pyridyl)-5-(3-pyridyl)-1,2,4-triazole is obtained which melts 143°–144.5°C.

EXAMPLE 25

1-n-PROPYL-3,5-BIS(4-PYRIDYL)-1,2,4-TRIAZOLE

To 3,5-bis(4-pyridyl)-1,2,4-triazole (4.4 g., 0.02 mole) in dry tetrahydrofuran (200 ml.) is added 57% sodium hydride in mineral oil (1 g. 0.024 mole) and the mixture is heated 45 minutes at reflux. The suspension is concentrated to a solid, N,N-dimethylformamide (70 ml.) and n-propyl iodide (0.022 mole) are added. The mixture is stirred 0.5 hour at ambient temperature followed by heating on the steam bath for 4 hours. The solution is concentrated to a gum, water is added and the material solidifies. Following recrystallization from methylcyclohexane there is obtained 1-n-propyl-3,5-bis(4-pyridyl)-1,2,4-triazole, m.p. 88°–89.5°C.

EXAMPLES 26 – 30

Following substantially the same procedure described in Example 25 but replacing the n-propyl iodide by an equimolecular quantity of the alkylating agent identified in column 2 of the following table, the 1-$R_1$-3,5-bis(4-pyridyl)-1,2,4-triazole compound having the $R_1$ substituent identified in column 3 is obtained.

| Example No. | Alkylating Agent | R₁ | Melting Point °C |
|---|---|---|---|
| 26 | Br—CH₂C≡CH | —CH₂C≡CH | 175.5–176.5 |
| 27 | Br—CH₂CH=CH₂ | —CH₂CH=CH₂ | 127–128.5 |
| 28 | I—CH₂CH₃ | —CH₂CH₃ | 139–140 |
| 29 | I—CH(CH₃)₂ | —CH(CH₃)₂ | 123.5–125.5 |
| 30 | I—(CH₂)₃CH₃ | —(CH₂)₃CH₃ | 88.5–89.5 |

Any departure from the above description which conforms to the present invention is intended to be included within the scope of the claims.

What is claimed is:

1. A compound of the formula:

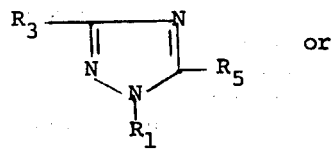 or

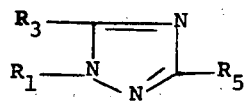

wherein $R_1$ is benzenesulfonyl;
$R_3$ is phenyl, lower alkylphenyl, tri-lower alkylphenyl, pyridyl, mono-lower alkylpyridyl or di-lower alkylpyridyl; and
$R_5$ is pyridyl, mono-lower alkylpyridyl or di-lower alkylpyridyl.

2. A compound having the formula:

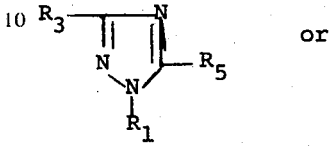 or

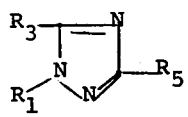

wherein $R_1$ is benzenesulfonyl;
$R_3$ is pyridyl, mono-lower alkylpyridyl, di-lower alkylpyridyl or an N-oxide thereof; and
$R_5$ is pyridyl, lower alkylpyridyl or an N-oxide thereof, such that one of $R_3$ and $R_5$ is an N-oxide.

3. A compound as claimed in claim 1 wherein $R_3$ and $R_5$ each represent 4-pyridyl.

* * * * *